United States Patent [19]
Valtuena et al.

[11] Patent Number: 5,830,455
[45] Date of Patent: Nov. 3, 1998

[54] METHOD OF TREATMENT USING A THERAPEUTIC COMBINATION OF α INTERFERON AND FREE RADICAL SCAVENGERS

[75] Inventors: Jesus Prieto Valtuena; Oscar Beloqui Ruiz, both of Pamplona, Spain

[73] Assignee: Glaxo Wellcome Inc., Research Triangle Park, N.C.

[21] Appl. No.: 706,645

[22] Filed: Sep. 6, 1996

Related U.S. Application Data

[63] Continuation of Ser. No. 170,735, Dec. 21, 1993, abandoned.

[30] Foreign Application Priority Data

Dec. 22, 1992 [GB] United Kingdom ................ 9226729.3

[51] Int. Cl.$^6$ .................................................. A61K 38/21
[52] U.S. Cl. .......................... 424/85.4; 424/85.7; 514/18
[58] Field of Search ................................. 424/85.4, 85.7; 514/18

[56] References Cited

U.S. PATENT DOCUMENTS

| | | | |
|---|---|---|---|
| 4,100,150 | 7/1978 | Cartwright | 424/85.4 |
| 4,762,705 | 8/1988 | Rubin | 424/85 |
| 4,927,762 | 5/1990 | Darfler | 435/240.31 |
| 4,985,241 | 1/1991 | Zimmerman et al. | 424/85.1 |
| 5,080,906 | 1/1992 | Carenzi et al. | 424/452 |
| 5,248,697 | 9/1993 | Wilmore | 514/563 |

FOREIGN PATENT DOCUMENTS

| | | |
|---|---|---|
| 0 486 912 | 5/1992 | European Pat. Off. . |
| 269017 | 7/1992 | European Pat. Off. . |
| 2 290 222 | of 1976 | France . |
| 1 526 205 | 9/1978 | United Kingdom . |
| 2 192 789 | 1/1988 | United Kingdom . |

OTHER PUBLICATIONS

Bisceglie et al., N. Eng. J. Med., vol. 321 (22), pp. 1506–1510, 1989.
Van der Nuy, Pharm. Weekbl., vol. 121(29), pp. 646–649, 1986.
Jose Vina et al., Br. J. Nutr., vol. 62(3), pp. 683–691, 1989.
Wells, Prog. Clin. Biol. Res., vol. 135, pp. 367–371, 1983.
Bridgeman et al., Thorax, vol. 46(1), pp. 39–42, 1991.
Beloqui, O et al., J. Interferon Res., vol. 13, pp. 279–282, 1993.
Ahezzi et al., Cancer Res., vol. 45, pp. 3444–3447, 1985.
Ahezzi et al., J. Interferon Res., vol 6, pp. 251–256, 1986.
Schor, "Mechanisms of Synergistic Toxicity of the Radioprotective Agent, WR2721, And 6–Hydroxydopamine", Biochemical Pharmacology 37(9):1751–1762 (1988).
Tabachnik et al, "Studies on the Reduction of Sputum Viscosity in Cystic Fibrosis Using an Orally Absorbed Protected Thiol", The Journal of Pharmacology and Experimental Therapeutics 214(2) 246–249 (1980).
Shirota et al, "Failure of glutathione and cystein prodrugs to block the chlorpropamide–induced inhibition of aldehyde dehydrogenase in vivo", Biochemical Pharmacology 43(4):916–918 (1992).
Porta et al, "L–2–Oxothiazolidine–4–Carboxylic Acid, a Cysteine Prodrug: Pharmacokinetics and Effects on Thiols in Plasma and Lymphocytes in Human", The Journal of Pharmacology and Experimental Therapeutics 257(1):331–334 (1991).
Hazelton et al, "Effects of Cysteine Pro–Drugs on Acetaminophen–Induced Hepatotoxicity", The Journal of Pharmacology and Experimental Therapeutics 237(1):341–349 (1986).
Trepo et al, "Treatment of chronic hepatitis C", Therapy in Liver Diseases, pp. 253–258 (1992), eds J. Rodes/V. Arroyo, Ediciones Doyma SA.
Roederer M. et al., *Aids Research and Human Retroviruses*, vol. 8 No. 2 (1992) pp. 209–217.
Kitamura Y. et al., *The Journal of Pharmacology and Experimental Therapeutics*, vol. 25–No. 2 (1988) pp. 667–671.
Roberts J.C. et al., *J. Med. Chem.*, vol. 30 (1987) pp. 1891–1896.

*Primary Examiner*—Chhaya D. Sayala
*Attorney, Agent, or Firm*—Nixon & Vanderhye P. C.

[57] ABSTRACT

The present invention relates to a therapeutic combination therapy involving the use of human interferon. The therapy involves the treatment of conditions susceptible to treatment with human interferon, with a combination of a human interferon and a free radical scavenger or precursor or inducer.

7 Claims, 4 Drawing Sheets

METHOD OF TREATMENT USING A THERAPEUTIC COMBINATION OF α INTERFERON AND FREE RADICAL SCAVENGERS

This is a continuation of application Ser. No. 08/170,735, filed Dec. 21, 1993, now abandoned.

FIELD OF THE INVENTION

The present invention relates to a therapeutic combination, more particularly a combination therapy involving the use of human interferon.

BACKGROUND OF THE INVENTION

The first and localized response of an animal to a virus infection is to produce the lymphokine interferon. Originally thought to be a single molecule, interferons are now recognized as a large family of proteins, old in evolutionary terms, and widely distributed in the animal kingdom. Although there may be some limited cross-reactivity, interferons are generally species specific. Three types of interferon have been characterized originally known as leukocyte, fibroblast and immune interferon and now designated interferons α, β and γ respectively.

Human interferon-α can be produced by many different cell types, and HPLC has resolved this type of interferon into over 30 subtypes each coded by a different gene. Human interferon-β is generally considered to be a single substance and is made by fibroblasts. Human interferon-γ is also a single substance made by helper-induced subsets of T-lymphocytes on exposure to antigen or by exposing human white blood cells, T-lymphocytes, or T-lymphoblastoid cells to mitogens.

Human interferon-α is manufactured in commercial amounts by stimulating the Namalwa human lymphoblastoid cell line with Sendai virus to produce a natural mixture of up to 22 subtypes of interferon-α which are then purified by chromatography to a purity of 95% and a specific activity of about $100 \times 10^6$ IU/mg protein. Such a product, identified as human interferon α-N1, is commercially available under the name WELLFERON (registered trademark of The Wellcome Foundation Limited). Natural human interferon-β is derived from human diploid fibroblasts, usually from neonatal tissue, production being induced for example by adding synthetic double stranded RNA. Human interferon-γ may be made from buffy coats, with a mitogen such as *Staphylococcus enterotoxin A* as inducer.

Human interferons-α, -β and -γ can also be produced using recombinant DNA technology although when produced by expression of the relevant gene in bacterial cells, recombinant interferons may not have the same tertiary structure as the natural molecules. Similarly, interferons produced in bacterial cells will not be glycosylated and although this does not appear to affect the biological activity of the molecule when tested in vitro, it could alter conformation and antigenicity and may influence tested in vitro, it could alter conformation and antigenicity and may influence distribution in the body. Such a recombinant human interferon preferably possesses greater than 90% amino-acid homology with a natural human interferon; more preferably 95% homology, yet more preferably 97% homology, yet more preferably 98% homology, yet more preferably 99% homology and most preferably 100% homology. Recombinant human interferons are available commercially and examples are interferon α-2a (ROFERON-Roche) and interferon α-2b (INTRON-Schering). These molecules differ by a single amino acid residue at position 23 (lysine in ROFERON and arginine in INTRON).

Human interferons have been used for some years in the treatment of hepatitis. The first trials in the mid 1970s used human leukocyte interferon produced from buffy coat cells left over after the production of plasma from donated blood and this necessarily limited the quantity available. In the early 1980s advances in production techniques led to the use of both natural and recombinant human interferon-α or the treatment of chronic hepatitis B. While this treatment can be regarded as successful in many cases, response rates to treatment with human α-interferons alone, as judged by sustained loss of viral markers, are generally considered to be less than 50%. Human interferons-β and -γ have also been investigated for use in chronic hepatitis B but have not become established treatments.

All three types of human interferon have also been investigated in the therapy of chronic hepatitis C although low availability of interferon-β has limited work with this type of interferon. Quite extensive trials have been carried out using the α-interferons referred to above (Interferon α-2a, interferon α-2b and lymphoblastoid interferon) and results have been encouraging in that complete response occurs in about 40% of patients. However, relapse rates of about 50% have been observed 6 months after treatment so that only 20 to 25% of patients may benefit in the long term.

For a complete review of the use of interferons in the treatment of hepatitis, reference can be made to the book "Interferons in the Treatment of Chronic Virus Infection of the Liver" by Eddleston and Dixon, Pennine Press. 1990.

In addition, interferons have been proposed for use in the therapy of a number of other conditions including viral diseases other than hepatitis, disorders involving the immune system, including autoimmune conditions, and cancers of various sorts including renal cancer, breast cancer, colon cancer, Kaposi's Sarcoma, glioma and malignant hematological conditions.

There is some evidence, particularly in the context of HIV, to suggest that chronic viral infections may cause oxidative stress in the infected organism. Induction of oxidative stress by viruses may be due to a variety of mechanisms including activation of phagocytic cells by immunocomplexes, promotion of free radical formation by pro-inflammatory cytokines (TNFα, IL6) and generation of reactive oxygen species by direct interaction between viral surface glycoproteins and cell membranes.

A number of substances are known which act as free radical scavengers at the level of the cell or the whole organism. For example reduced glutathione is a widely distributed non-protein thiol present in most mammalian cells which has been implicated in a variety of metabolic functions including detoxification reactions against free radicals. Glutathione is the main intracellular defence mechanism against oxidative stress and factors that increase free radical formation lead to consumption of intracellular glutathione stores. Glutathione also plays an important immunoregulatory role in modulating lymphocyte activation and proliferation, T-cell cytotoxicity and macrophage-lymphocyte interactions.

N-acetyl cysteine has been known for many years as a mucolytic, a corneal vulnary and as an antidote to acetaminophen poisoning. The compound has a relatively mild reducing effect and is thought to act as a mucolytic by splitting disulphide bonds in mucoproteins. There have been a number of reports that reduced glutathinone levels may be lowered in some chronic viral conditions, in particular HIV infections. N-acetyl cysteine is a precursor and thus an inducer of glutathione and N-acetyl cysteine has been proposed as a therapeutic agent for use in the case of HIV infection.

EP-A-0 269 017 (Cetus) relates to the combination of a lymphokine or cytotoxin and a free radical scavenger or metabolic inhibitor for the treatment of biological damage to mammalian hosts caused by free radical production. Although the specification refers in passing to interferons as the lymphokine and also mentions infections as a possible cause of biological damage the specification is essentially concerned with free radicals which may be generated during the treatment of cancer. The biological data given in the specification relate entirely to cancer and are concerned mainly with the administration of TNFα in murine fibrosarcoma.

SUMMARY OF THE INVENTION

The present invention relates to the use of a free radical scavenger or a precursor or inducer thereof as an adjunct to therapy with a human interferon.

Thus according to one aspect, the present invention provides a method for the treatment of a patient suffering from a condition susceptible to therapy with an interferon which comprises administration to the patient of an effective amount of a human interferon, and wherein a free radical scavenger or a precursor or inducer thereof is also administered for all or part of the duration of the administration of the human interferon.

According to another aspect, the invention provides the use of a human interferon for the manufacture of a medicament for use in the treatment of a condition susceptible to therapy with an interferon by a method wherein a free radical scavenger or a precursor or inducer thereof is also administered for all or part of the duration of the administration of the human interferon.

According to a still further aspect, the invention provides the use of a free radical scavenger or a precursor or inducer thereof for the manufacture of a medicament for the treatment of a condition susceptible to therapy with an interferon by a method involving administration of a human interferon and wherein the free radical scavenger or a precursor or inducer thereof is also administered for all or part of the duration of the administration of the human interferon.

The condition susceptible to therapy with an interferon may be any of the conditions for which human interferons have become established or have been proposed as effective treatments. Such conditions include viral infections, such as viral hepatitis, infections caused by human papilloma virus, cytomegalovirus and HIV, non-viral infections such as tuberculosis, and conditions such as asthma.

The present invention is particularly applicable to the use of human interferons in the therapy of hepatitis. As already indicated, although such therapy is of considerable benefit in many cases, the response rate is relatively low and in the case of hepatitis C there is a substantial rate of relapse. Accordingly, there is a considerable need for improvements in the therapy of hepatitis with human interferon to overcome these problems.

Examples of human interferon of use with the present invention include those mentioned hereinbefore.

According to another aspect, the present invention provides a method for the treatment of a viral hepatitis infection by administration of a human interferon, wherein a free radical scavenger or a precursor or inducer thereof is also administered for all or part of the duration of the administration of the human interferon.

According to a further aspect, the invention provides potentiated combinations also known as synergistic combinations, of a human interferon and a free radical scavenger or precursor or inducer thereof for use in the treatment of a condition susceptible to therapy with an interferon. The active ingredients of potentiated combinations of the invention may be administered concurrently or sequentially as separate formulations or as a single combined formulation. If there is sequential administration, the delay in administering the second of the active ingredients should not be such as to lose the benefit of a potentiated therapeutic effect of the combination of the active ingredients.

The present invention is applicable to the treatment of viral hepatitis in all of its forms, five types now being recognised designated hepatitis A, B, C, D, and E respectively.

Hepatitis A is an acute viral infection with an incubation period of under 40 days transmitted by the fecal-oral route. The virus is a member of the picomavirus family and consists of a 27 nm spherical, non-enveloped particle. The viral genome has been sequenced and comprises a single strand of RNA containing ca. 7480 bases.

Hepatitis B is a universal and serious virus disease with an estimated over 200 million carriers world wide. When it was known as serum hepatitis, the disease was diagnosed on the basis of the appearance of symptoms 2 to 3 months after blood transfusion, the injection of human plasma fractions or the use of unsterilised needles of syringes. The recognition of serum markers for hepatitis B has confirmed the importance of skin penetration and in particular blood in the transmission of the virus. Following the acute phase of the disease, the majority of adult patients recover spontaneously within a matter of weeks but a proportion do not clear the virus after many months and become chronic carriers. Hepatitis B virus belongs to the hepadna virus family whose genome consists of a small, incompletely double-stranded circular piece of DNA that replicates by copying its DNA into RNA and then re-copying the RNA to DNA using reverse transcriptase.

Non-A, non-B hepatitis is being recognized as an increasingly serious international health problem. At least 80% of cases of chronic post-transfusional non-A, non-B hepatitis have been shown to be due to the virus now identified as hepatitis C and this virus probably accounts for virtually all cases of post-transfusional hepatitis in clinical settings where blood products are screened for hepatitis B. Whereas approximately half of the cases of acute hepatitis C infection resolve spontaneously over a period of months, the remainder become chronic and in many if not all such cases chronic active hepatitis ensues with the potential for cirrhosis and hepatocellular carcinoma. The structure of the hepatitis C virus genome has recently been elucidated and the virus has been characterized as a single stranded RNA virus with similarities to flaviviruses.

Hepatitis D virus was first recognised in 1977 following identification of a novel antigen in certain carriers of hepatitis B. The virus requires hepatitis B (or a closely related hepadna virus) as a helper virus to replicate although replication is sufficiently efficient that it can attain a higher titer than the helper virus in the serum. The hepatitis D genome consists of covalently closed circular RNA and has some structural similarity to certain circular viroids or virus-like agents found in plants. Hepatitis D infection is associated with aggressive liver disease and is more often found in patients with severe disease (chronic active hepatitis or cirrhosis) than in those with chronic persistent hepatitis.

Hepatitis E virus is related to the virus which causes Hepatitis A (Reyes et al., Science 247, 1335–1339 (1990)) and produces an acute form of hepatitis with no chronic phase. The virus is enteric, water borne and normally transferred by the fecal/oral route. It is particularly prevalent in the Indian sub-continent and produces a high mortality rate in pregnant women.

The present invention is also applicable to the treatment of human papilloma virus which is the agent responsible for non-genital warts, juvenile laryngeal papilloma, condyloma accuminata and which is involved in cervical cancer. The invention is also applicable to accuminata and which is involved in cervical cancer. The invention is also applicable to the treatment of other viral infections such as three caused by human cytomagalovirus and HIV. The invention is also applicable to the treatment of non-viral infections such as tuberculosis and conditions such as asthma.

DETAILED DESCRIPTION OF THE INVENTION

The human interferon for use according to the invention may be any of the three types referred to above, i.e. interferon-α, interferon-β or interferon-γ. Generally the human interferon will be interferon-α or interferon-γ. Preferably the human interferon is human interferon-α, more preferably human interferon-α derived from a human cell line in culture or a recombinant human interferon-α. According to one preferred embodiment, the human interferon is recombinant interferon α-2a or interferon α-2b, for example one of the products marketed under the trade names ROFERON and INTRON. According to another particularly preferred embodiment, the human interferon is human lymphoblastoid interferon (interferon αN1), for example the product marketed by The Wellcome Foundation Ltd. under the trademark WELLFERON.

The term 'human interferon' is intended to include any wild-type interferon, the sequence of which was determined from a human, and any allele, variant or mutant thereof which substantially conserves the activity of the corresponding wild-type sequence and which possesses greater than 80% sequence homology with the corresponding wild-type sequence.

Human interferons may be formulated for administration according to the invention in the same manner as for use alone in the treatment of the condition in question, for example hepatitis. Thus the interferon is generally administered parenterally, for example by injection, preferably subcutaneous injection. Preferably the interferon is formulated as an aqueous preparation or as a lyophilized product intended for reconstitution with a suitable vehicle, for example water for injection. The formulation may also contain a suitable carrier diluent or stabilizer, for example another human protein such as human serum albumin.

The human interferon will generally be administered in accordance with the treatment protocols already established for the product in question. For example human interferon-α whether lymphoblastoid or recombinant, may be administered at a dose of 1 to 10 Mega Units of interferon per day. The dose may be administered on 3 or more days per week, preferably 3 times per week. A preferred dose range is 2 to 6 Mega Units of interferon per day on 3 or more days per week, preferably 3 times per week, and particular doses of interferon are 5 Mega Units or, most preferably, 3 Mega Units per day or 3 or more days per week, preferably 3 times per week. In the treatment of hepatitis, the duration of administration of the interferon is usually a period of several weeks, for example 12 to 30 weeks, in particular about 24 weeks, although longer periods of treatment of up to a year or more may be appropriate in some cases.

As used herein, the term "free radical scavenger or precursor or inducer thereof" means any material which is capable, on administration to a host, of reducing the level of free radicals (also referred to as oxidative stress) within the host. The material may bring about this reduction in the level of free radicals by direct scavenging of free radicals or by inducing, whether as a direct biological precursor or otherwise, the production within the host of a material having a scavenging effect on free radicals. Alternatively, the material may reduce the level of free radicals by exerting an inhibiting effect in the processes which lead to the generation of free radicals.

Preferred free radical scavengers or precursors or inducers thereof include glutathione and precursors thereof such as derivatives of the naturally occurring amino acid cysteine. One particularly preferred precursor of glutathione is N-acetyl cysteine. As indicated above, N-acetyl cysteine already has an established pharmaceutical use as a mucolytic and pharmaceutical preparations of the compound are available commercially. Other free radical scavengers or precursors or inducers thereof include vitamin A, vitamin C (ascorbic acid), vitamin E, uric acid, buthionine sulphoxime diethyl maleate metronidazole, superoxide dismutase and methionine. Materials which inhibit the generation of free radicals include inhibitors of xanthine oxidase such as allopurinol and are considered to be "free radical scavengers or precursors or inducers thereof" as referred to herein.

The free radical scavenger or precursor or inducer thereof should be administered in a form and dose such that it is capable of reducing free radical generation and/or relieving the effects of free radical generation (oxidative stress) in the host. Administration may be by any convenient route, for example oral or parenteral, depending on the nature of the material. Oral administration is preferred where possible.

N-acetyl cysteine is preferably formulated for oral administration in the form of tablets or granules or as a liquid preparation, for example a syrup. An appropriate dose of N-acetyl cysteine is in the range 200 mg to 4 g per dose administered up to 4 times per day, for example 400 to 800 mg administered 4 times per day, preferably 600 mg administered 4 times per day.

Although the therapy provided according to the invention, for example for viral hepatitis, consists of the combined administration of a human interferon and a free radical scavenger or precursor or inducer thereof, the two medicaments will generally be administered as separate preparations. However, in some circumstances, there may be an advantage in administering the two components as a combined preparation and the invention extends to such combined preparations.

Thus according to a further aspect the invention provides a pharmaceutical composition comprising a human interferon together with a free radical scavenger or a precursor or inducer thereof.

In general any such combined preparation with be in a form intended for parenteral administration, for example injection. Such a combined preparation may be presented in liquid form or in a solid form, with the human interferon lyophilized, and suitable for reconstitution into a liquid form.

It may also be appropriate to present the two medicaments together in a suitable form for separate administration. According to another aspect the invention provides a twin pack comprising in association for separate administration a human interferon and a free radical scavenger or a precursor or inducer thereof.

The present invention is particularly applicable to the therapy of hepatitis B or hepatitis C. As indicated above, administration of human interferon, particularly recombinant or lymphoblastoid interferon-α is already an established therapy for hepatitis B. In addition, a number of trials have indicated that the same therapy is also of considerable benefit in the treatment of hepatitis C. According to the present invention, therapy of patients suffering from hepatitis, in particular hepatitis B or hepatitis C, with interferon will be carried out essentially in accordance with the established protocols with the addition of treatment with a free radical scavenger or a precursor or inducer thereof for all or part of the duration of therapy with the human interferon.

Serum alanine aminotransferase (ALT) levels are a highly sensitive marker for liver dysfunction. Hepatitis B and hepatitis C infections are both characterized by raised ALT levels and the progress of the disease is generally monitored by determination of serum ALT. As indicated above, only about 50% or less of patients with hepatitis B or hepatitis C respond to treatment with human interferon-α in as demonstrated by a significant clearing of viral markers or lowering of ALT levels.

According to one embodiment of the invention, which is particularly applicable to the treatment of hepatitis B or hepatitis C. most particularly hepatitis C, treatment with human interferon, particularly human interferon-α, is undertaken in the usual manner for a period of several weeks, for example 12 to 30 weeks, in particular about 24 weeks. For patients who fail to respond to this initial course of treatment with human interferon as demonstrated by significantly reduced serum ALT levels, treatment is continued with the human interferon and with the additional treatment with the free radical scavenger or a precursor or inducer thereof, preferably glutathione or a precursor or inducer thereof, most preferably N-acetyl cysteine. Treatment with the human interferon and the free radical scavenger or precursor or inducer thereof may be continued for a further period of several weeks, for example 12 to 30 weeks, in particular about 24 weeks. In accordance with a preferred embodiment of the invention, this treatment protocol is applied to the treatment of hepatitis C with human lymphoblastoid interferon (human interferon α-N1).

As also indicated above, certain patients with hepatitis B or hepatitis C may respond initially to treatment with human interferon, particularly human interferon-α, but may subsequently relapse. Such patients may also benefit from a combined course of treatment with the human interferon and the free radical scavenger or a precursor or inducer thereof as outlined above.

It should be understood that doses of the human interferon and the free radical scavenger or a precursor or inducer thereof will vary depending on the patient and the precise condition from which the patient is suffering. Ultimately, the treatment will be under the control of and will be the responsibility of the attendant physician.

The invention is further illustrated by the following pilot study which should not be regarded as in any way limiting on the scope of the invention.

EXAMPLE

1. Introduction

Hepatitis C virus (HCV) is responsible for most cases of postransfusional and sporadic non-A, non-B hepatitis. Chronification of the infection is very common, leading to chronic hepatitis, cirrhosis and, ultimately, malignant degeneration.

Several controlled studies have shown that α-interferon (IFN) is useful in the treatment of chronic hepatitis C (CHC), but the response rate averages 50% and the frequency of relapse, after IFN cessation, may reach 30–40%. Accordingly, the proportion of patients with CHC sustaining normal transaminase levels after IFN withdrawal is only around 20–40% of all treated cases.

Reduced glutathione (GSH) is an important antioxidant in mammalian cells, being implicated in a great variety of cellular functions and it has been suggested that depletion of GSH may play a pathogenic role in some chronic viral diseases, such as AIDS. In this study GSH levels were measured in plasma and in peripheral blood mononuclear cells (PBMC) from patients with CHC who failed to respond to IFN therapy after at least 4 months of treatment. The effect of N-acetyl cysteine, a precursor of the thiol, was also evaluated on GSH levels and on the clinical and virological response to IFN therapy.

2. Patients and Methods 2.1 Patients

Fourteen patients (13 males and 1 female, mean age 51 years, range 27–71) diagnosed as suffering from CHC by histological and serological criteria, two of them with associated cirrhosis, were entered into the study. All of the patients had been under treatment with α-lymphoblastoid interferon (Wellferon) for a minimum period of 4 months (15±1.6 MU per week, range 9–21 MU per week); all patients showed abnormal ALT values (above 30 IU/L) when entered into the study. Most patients with CHC responding to IFN, normalize transaminase levels within the first 3 months of therapy and those who persist with high ALT values after 4 months of treatment can be considered to be non-responders. Accordingly, all patients in the present study were considered to be non-responders to IFN. Patients in the present study continued essentially the same IFN regimen as they had followed previously but added oral N-acetyl cysteine (NAC), 600 mg every 8 hours daily. No patient increased the interferon dosage after the addition of oral NAC, although in 3 cases the amount of interferon was slightly reduced (15±1.8 MU/week before NAC versus 11.5±1.3 MU/week after NAC).

In addition 10 patients (8 males and 2 females, mean age 32 years, range 24–63) recently diagnosed as suffering from having chronic hepatitis C, who had never received antiviral treatment took the same amount of oral NAC, but without interferon, over a period of one month.

Twenty-six healthy subjects (14 males and 12 females, mean age 43 years, ranging from 25 to 79) served as control group. All patients gave written informed consent and the study was approved by the Local Ethics Committee.

2.2 GSH determination in PBMC and Plasma

Blood samples for simultaneous determinations of GSH in PBMC (L-GSH) and in poor-platelet plasma (P-GSH) were obtained from each patient. PBMC were isolated by centrifugation on Lymphoprep (Nycomed Pharma AS, Oslo, Norway) and washed five times. Isolated cells were killed with 20% perchloric acid (2% final concentration), and after centrifugation (1200 g×10 minutes at 4° C.), and supernatants stored at −40° C., until use. Twenty percent perchloric acid was added to the poor platelet plasmas (2% final concentration), and after centrifugation, the supernatants were kept at −40° C. until GSH determination.

Stored samples were thawed and GSH determined following the enzymatic method described by Brigellus et al., Biochem. Pharmacol., 32, 2529–2534 (1983) as modified by Ferrer et al., Biochem. J., 264, 531–534 (1990). GSH, in the presence of GSH-S-transferase, is conjugated with 1-chloro-2,4-dinitrobenzene (CDNB)(SIGMA), and the absorbance of the complex measured at 340 nm using a Perkin-Elmer Lambda 2 spectrophotometer. Absolute values of GSH were obtained using a molar extinction coefficient of $9.6 \times 10^3$.

2.3 Extraction of RNA and RT-PCR

Reverse transcription polymerase chain reaction (RT-PCR) for HCV-RNA in serum and for either the positive or negative strands of HCV-RNA in PBMC was performed essentially as described by Ruiz et al., Hepatology, 16, 637–643 (1992) and Cheng et al., J. Hepatol., in press (1992). The procedures recommended by Kwoks and Higuchi, Nature, 339, 237–238 (1989), to reduce the risk of contaminations were strictly applied. All extractions and reactions were simultaneously carried out in positive and negative controls. An aliquot from the last washing of PBMC was also included, and PCR was always negative in these samples.

2.4 Statistical Analysis

All data are presented as means±standard error of mean (SEM). Comparisons for paired and impaired data were carried out using the Mann Whitney and Wilcoxon tests.

3. FIGURES

The results are described with reference to the accompanying drawings in which.

4. RESULTS

Figure 1:
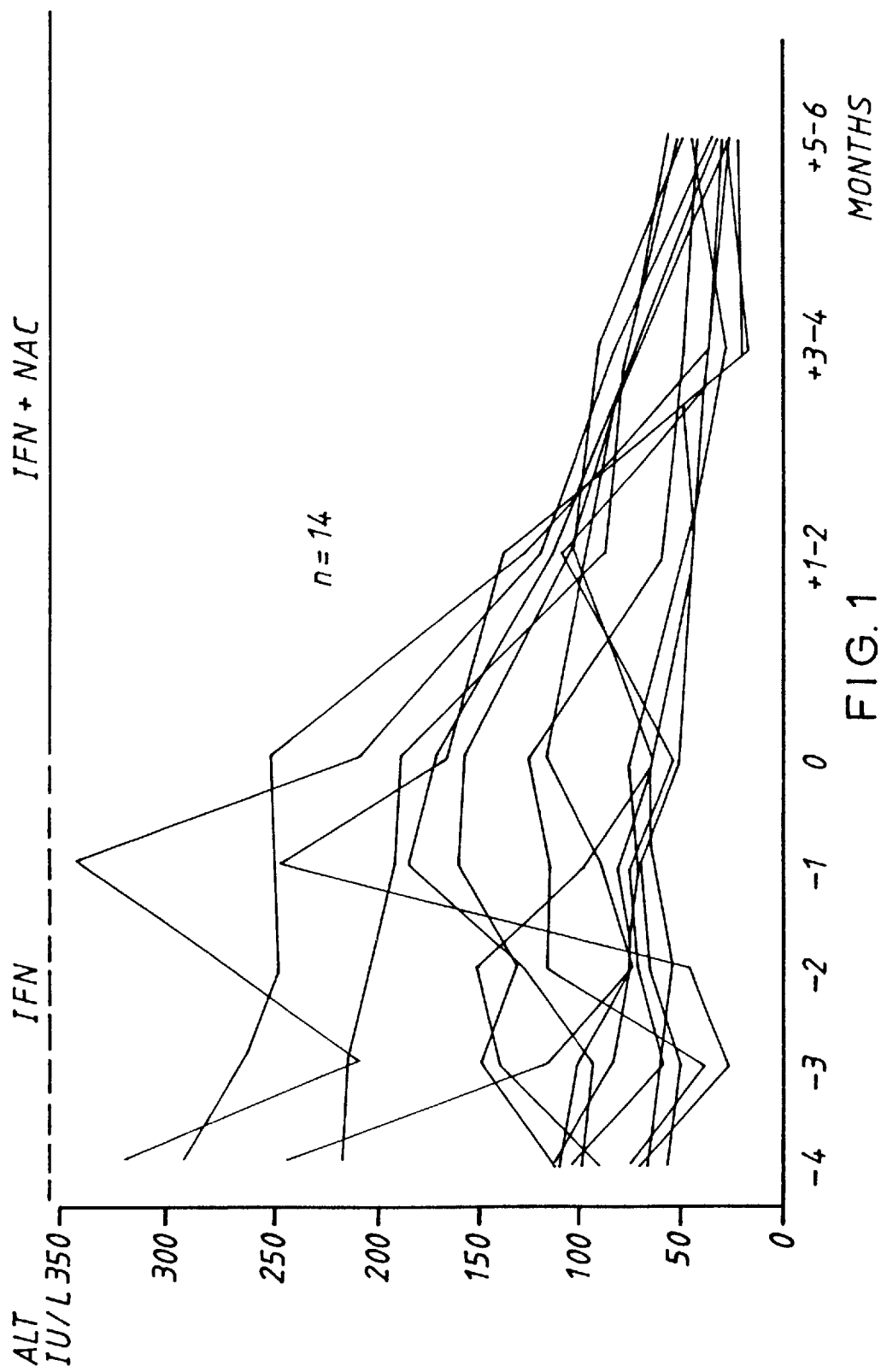
FIG. 1 shows the effect of IFN (−4 to 0 months) and IFN plus NAC (0 to 6 months) on ALT levels for the 14 patients entered into the study.

Mean serum ALT levels for the 14 patients entered into the study are shown in the following table which also shows L-GSH and P-GSH.

TABLE

| Month | Mean ALT (IU/L) | L-GSH (nMol/10$^6$ cells) | P-GSH ($\mu$M) |
| --- | --- | --- | --- |
| −4 | 139 ± 24 | — | — |
| 0 | 124 ± 24 | 1.45 ± 0.27 | 0.77 ± 0.21 |
| +1–2 | 87 ± 9 | — | — |
| +3–4 | 53 ± 7 | 3.32 ± 0.18 | 2.40 ± 0.20 |
| +5–6 | 37 ± 3 | — | — |

Values for L-GSH and P-GSH for the control group were as follows:

L-GSH 3.43±0.89 nMol/10$^6$ cells

P-GSH 18.1±4.08 $\mu$M.

In patients with chronic hepatitis C who had never received antiviral treatment (n=10), GSH levels in plasma (0.63±0.07 $\mu$M) and in PBMC (1.02±0.09 nMol/10$^6$ cells) appeared severely depressed in comparison with healthy controls (18.1±4.08 $\mu$M and 3.43±0.89 nMol/10$^6$ cells respectively, $P<0.01$). The administration of NAC during 1 month significantly increased the levels of GSH in PBMC (2.22±0.38 nMol/10$^6$ cells, $P<0.05$) but GSH in plasmas was not significantly modified (0.99±0.22 $\mu$M, n.s). In addition, the levels of serum ALT (128±32 IU/L versus 110±29 IU/L after one month of therapy with NAC) were also not significantly modified.

In patients not responding to interferon, GSH levels in PBMC (1.45±0.27 $\mu$Mol/10 cells) and in plasma (0.77±0.21 $\mu$M) also appeared significantly depressed in comparison with control values ($p<0.01$). In these patients, the administration of NAC together with interferon over a period of 3.4 months resulted in a significant elevation of GSH in mononuclear cells (3.32±0.18 nMol/10 cells, $p<0.05$) and in plasma (2.40±0.20 $\mu$M, $p<0.05$).

Figure 4:
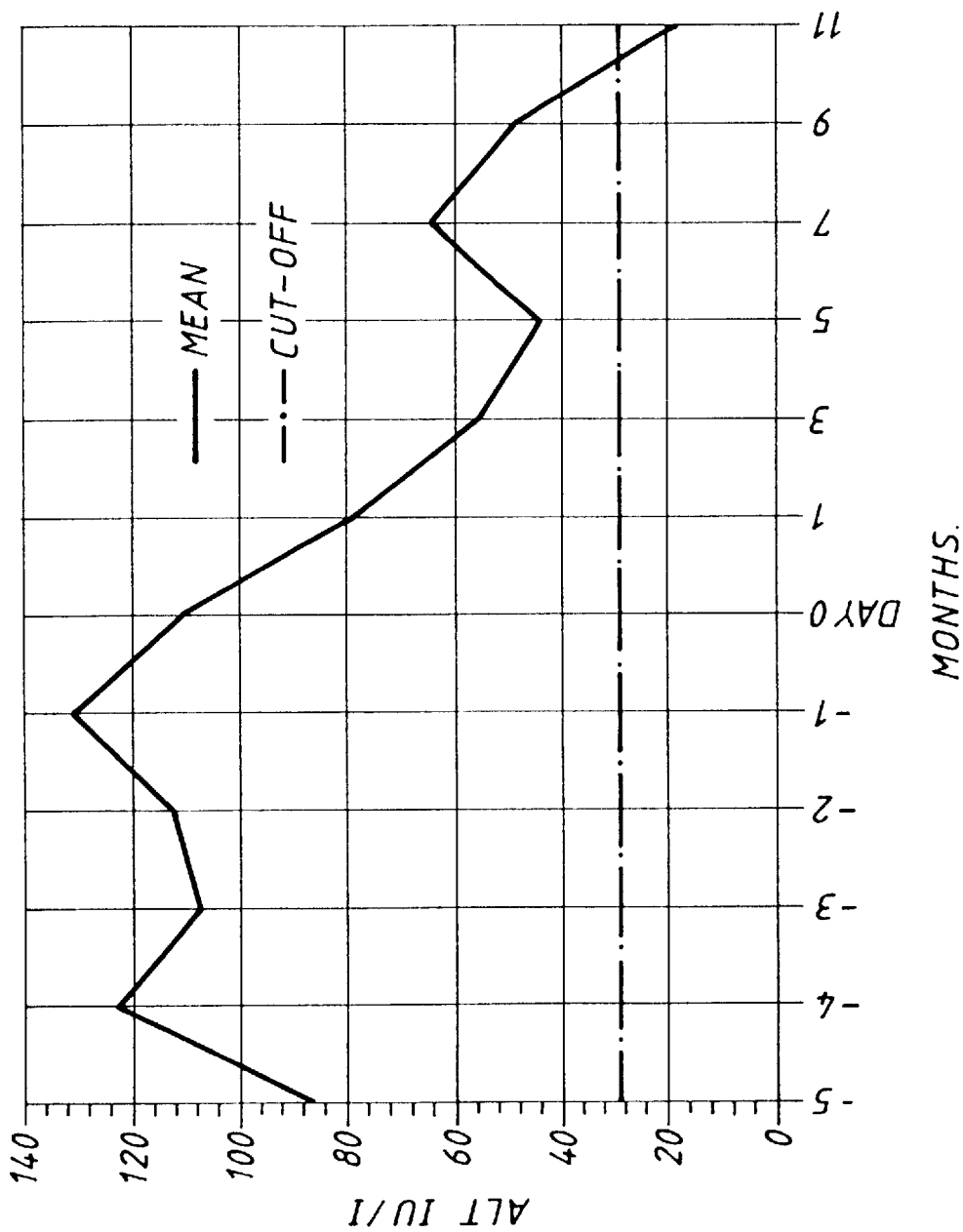
FIG. 4 shows ALT levels in the patients described in FIG. 1 above, when followed-up to 11 months post-commencement of IFN plus NAC therapy.

FIG. 1 and the above Table show that in the patients entered into the study (non responders to interferon) ALT levels did not change significantly during 4 months of IFN therapy (139±24 versus 124±17 IU/L, n.s). However, the addition of oral NAC resulted in a prompt and significant decrease of ALT; even after only one month of the combined treatment ALT values had significantly decreased (87±9 IU/L, $p<0.05$). Moreover, continuous administration of IFN and NAC over a period of 5–6 months produced a further decline in ALT values in all cases (37+4 IU/L), reaching normal values in 41% of cases and near normal values (maximum of 56 IU/L in one case) in the remainder. The addition of NAC to the IFN regimen clearly improves the response to IFN in the case of patients previously classified as non-responders to IFN therapy. As can be seen in FIG. 4 this decline in ALT values has continued up to the most recent patient analysis, 11 months post-commencement of combination therapy.

Figure 2:
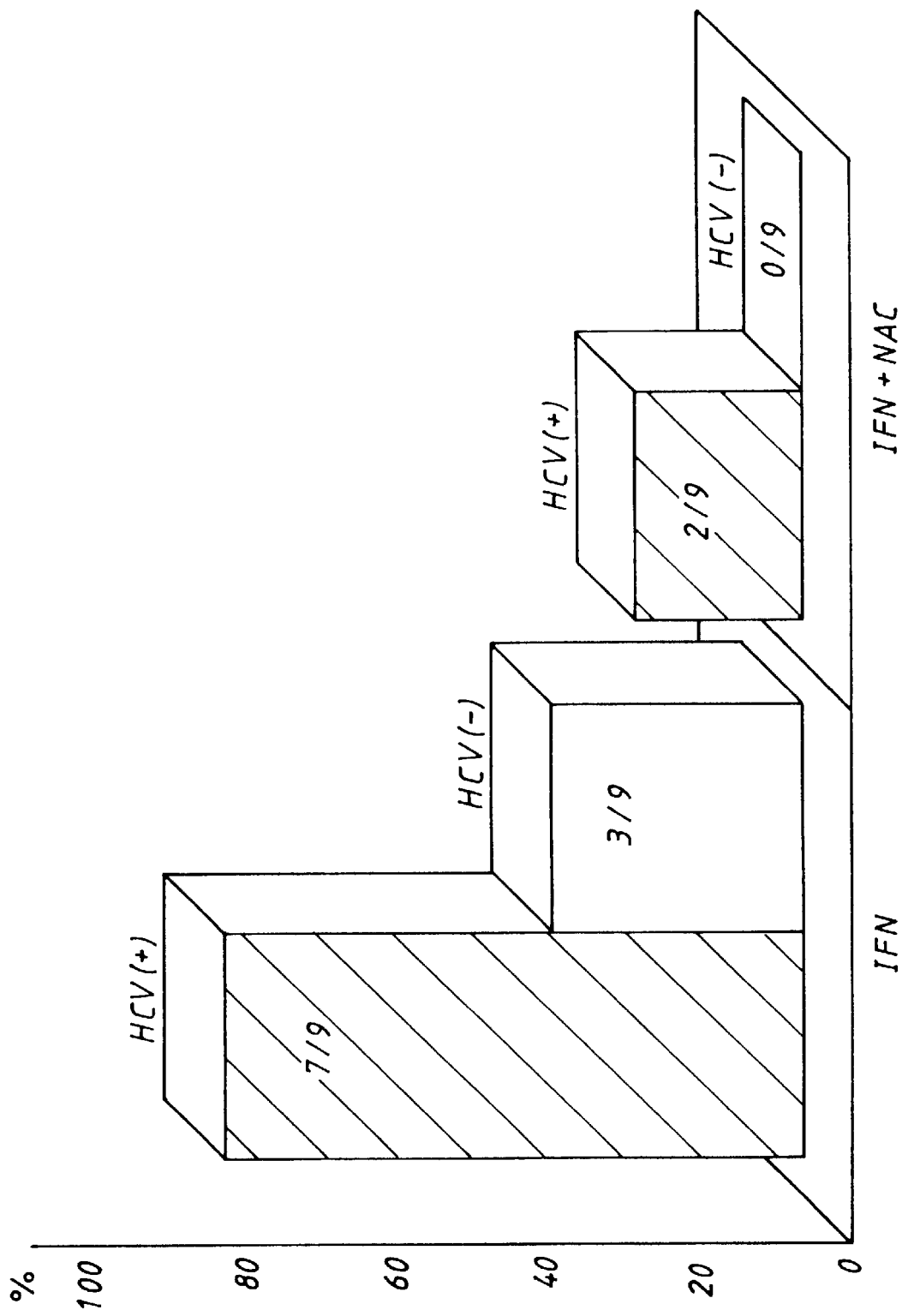
FIG. 2 shows the detection in PBMCs of positive and negative strands of HCV-RNA during treatment with IFN and with IFN plus NAC.

The reduction in ALT levels by the combination of IFN and NAC was accompanied by a concomitant effect on the replication of the virus. In the case of 9 patients classified as non-responders to IFN, PBMC were tested for the presence of both the genomic strand of HCV (positive RNA strand) and the replicative intermediate of the virus (negative RNA strand), before and after addition of NAC to the therapy. As shown in FIG. 2 when patients were being treated with IFN only, the genomic strand could be detected in 7 cases (77%), whilst the replicative intermediate was detected in 3 patients (33%). However, after 4–6 months of combined therapy with IFN and NAC, the positive strand was detected in only 2 cases (22%) and the negative HCV-RNA strand could not be detected in any of the cases.

Figure 3:
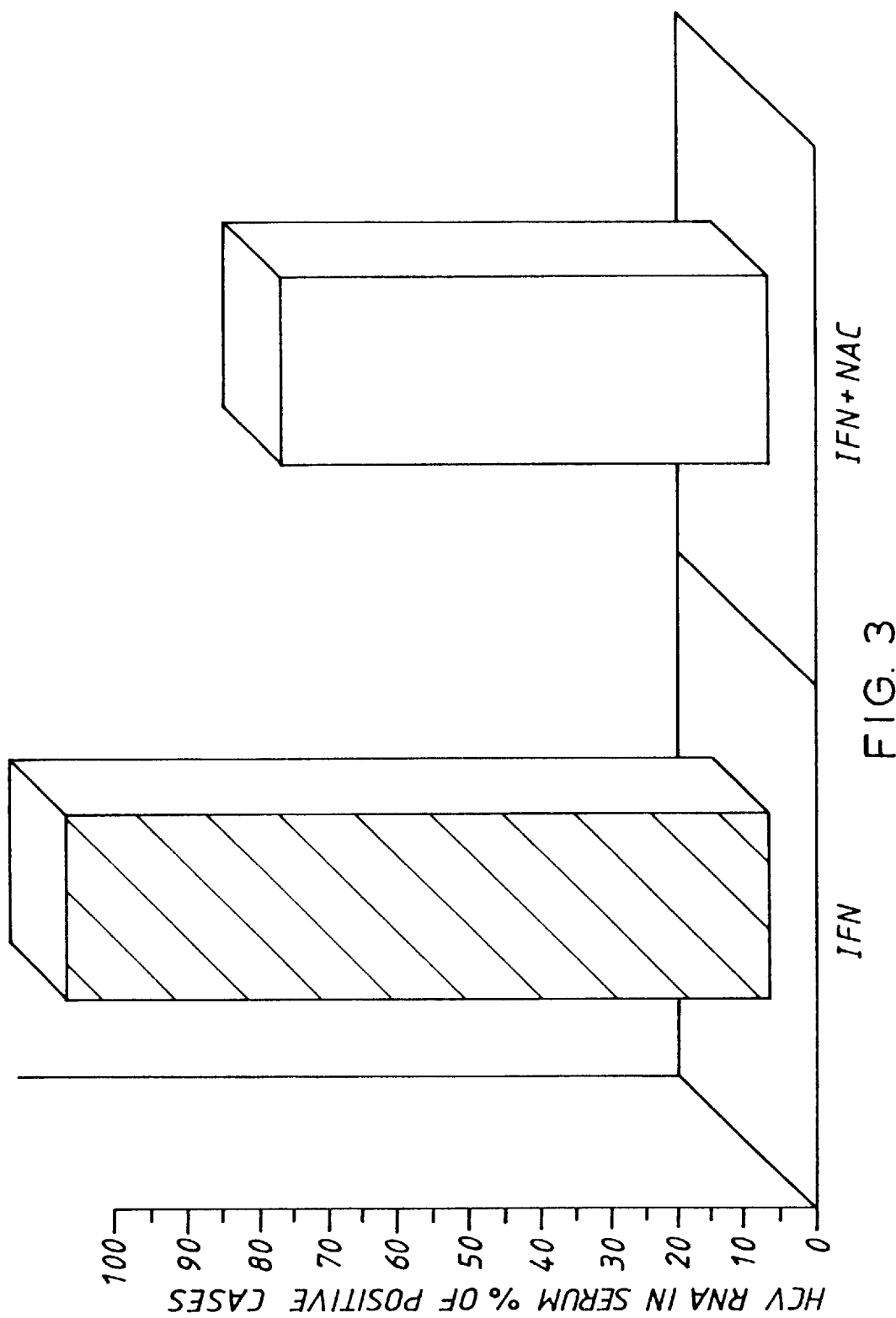
FIG. 3 shows the detection of HCV-RNA in serum at a serum dilution of 1:10 both before and after addition of NAC to the treatment with IFN.

Addition of NAC to the IFN regimen was also accompanied by decreased levels of HCV-RNA in serum. As shown in FIG. 3, after NAC addition of NAC to the therapy an increased concentration of serum was needed for HCV detection; thus, before NAC addition HCV-RNA could be detected in 100% of cases using a serum dilution of 1:10, whilst after addition of NAC to the therapy at the same serum dilution, the virus was detected in only 70% of patients.

We claim:

1. A method for the treatment of a patient suffering from chronic hepatitis C infection with a human interferon-α who has failed to respond to treatment with the human interferon-α which comprises treatment of the patient with effective amounts of the human interferon-α and a free radical scavenger or precursor or inducer thereof.

2. A method according to claim 1, wherein the human interferon-α is recombinant.

3. A method according to claim 1, wherein the human interferon-α is natural.

4. A method according to claim 3, wherein the natural human interferon-α is human lymphoblastoid interferon.

5. A method according to claims 1, 2, 3 or 4, wherein the free radical scavenger or precursor or inducer thereof is glutathione or a precursor or inducer thereof.

6. A method according to claims 1, 2, 3 or 4, wherein the free radical scavenger or precursor or inducer thereof is N-acetyl cysteine.

7. A method according to claim 1, wherein the patient has previously responded to treatment with the human interferon.

* * * * *